United States Patent [19]

Carney et al.

[11] 4,189,569
[45] Feb. 19, 1980

[54] SELDOMYCIN FACTOR 5 DERIVATIVES

[75] Inventors: Ronald E. Carney, Gurnee; James B. McAlpine, Libertyville, both of Ill.

[73] Assignee: Abbott Laboratories, Chicago, Ill.

[21] Appl. No.: 922,134

[22] Filed: Jul. 5, 1978

Related U.S. Application Data

[63] Continuation-in-part of Ser. No. 721,615, Sep. 8, 1976, abandoned.

[51] Int. Cl.$^2$ .................... A61K 31/71; C07H 15/22
[52] U.S. Cl. .................... 536/17 R; 424/180; 536/4
[58] Field of Search ........................................ 536/17

[56] References Cited

U.S. PATENT DOCUMENTS

| | | | |
|---|---|---|---|
| 3,868,360 | 2/1975 | Daniels et al. | 536/17 |
| 4,002,608 | 1/1977 | Wright et al. | 536/17 |
| 4,045,610 | 8/1977 | Nara et al. | 536/17 |
| 4,078,138 | 3/1978 | Akita et al. | 536/17 |

*Primary Examiner*—Johnnie R. Brown
*Attorney, Agent, or Firm*—Robert L. Niblack; Gildo E. Fato

[57] ABSTRACT

Described are novel derivatives of seldomycin factor 5 (XK-88-5) and particularly 3'-Epi-seldomycin factor 5, which exhibit improved activity against gram-positive and gram-negative bacteria resistant to aminoglycoside antibiotics, and a method of preparing them.

7 Claims, No Drawings

SELDOMYCIN FACTOR 5 DERIVATIVES

This application is a continuation in-part of application Ser. No. 721,615, filed Sept. 8, 1976, and now abandoned.

BACKGROUND OF THE INVENTION

Seldomycin factor 5 is a pseudotrisaccharide antibiotic elaborated by the microorganism *Streptomyces hofunensis* and for which the formula

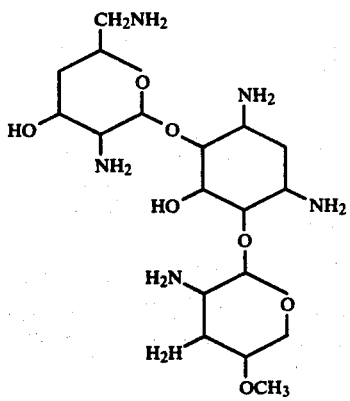

has been elucidated. Seldomycin factor 5 is also identified as XK-88-p5. It is a highly active antibiotic, effective against both gram-positive and gram-negative organisms such as *Staphlococcus aureus, Klebsiella pneumoniae, Escherichia coli,* and *Proteus, Enterobacter* and *Salmonella* species. Seldomycin factor 5 is only one of a number of antibiotics produced by the fermentation of *Streptomyces hofunensis*. The isolation and characterization of seldomycin factor 5 is described in U.S. Pat. No. 3,939,043, issued Feb. 17, 1976.

The nomenclature of the above formula is simplified by the following numbering system

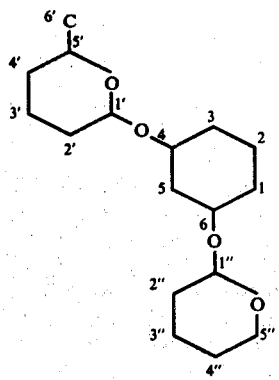

in which the carbons of the cyclitol moiety, also known as the 2-deoxystreptamine moiety, are numbered 1 through 6. The carbons of the hexose moiety are numbered with a single prime, 1' through 6', and the carbons of the pentose moiety are numbered with a double prime, 1" through 5".

Microorganisms are known to frequently acquire resistance to amino-glycoside antibiotics by a mechanisms known in the art as "R-Factors". Very generally an R-factor is the extrachromosomal genetic capability of bio-chemically modifying the antibiotic in such a way as to interfere with its antibacterial action, thereby enabling the organism to grow. Some of the known mechanisms of R-factor mediated resistance involve the attachment of a phosphate ester grouping to the hydroxyl group of Kanamycin or Neomycin analogous to the hydroxyl group at $C_3'$ in seldomycin factor 5. It is known in the art that inversion of configuration of an hydroxyl group will frequently overcome mechanisms of resistance involving the attachment of groups to that hydroxyl group. It is desirable to obtain compounds which exhibit a broad spectrum of activity against strains which are resistant to other aminoglycosides.

SUMMARY OF THE INVENTION

Described are seldomycin factor 5 derivatives of the following general formula:

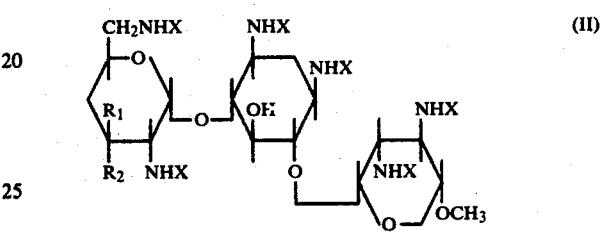

where $R_1=OH$ and $R_2=H$, or $R_1=H$ and $R_2=OH$, or $R_1=RSO_3$ and $R_2=H$, where R is alkyl of from 1-6 carbon atoms, aryl such as phenyl or substituted phenyl such as halophenyl, namely chloro, bromo, or fluoro phenyl, or nitrophenyl, toluyl or naphthyl, or benzyl and where X is a carbonyl containing amine-protecting group such as alkoxy carbonyl, aryloxy carbonyl and aralkyloxy carbonyl and compounds of the type of the following formula:

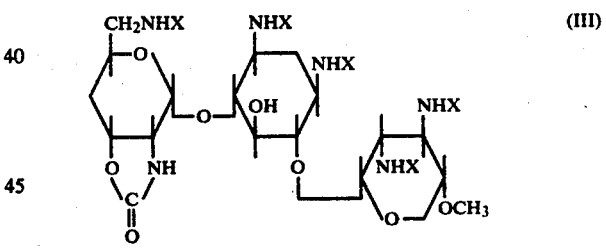

where X is an amine-protecting group as defined above and the compound having formula:

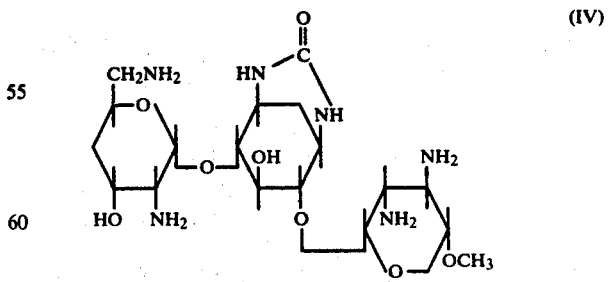

In particular, the invention relates to the derivative 3'-epi-seldomycin factor 5, which is effective against bacteria known to be resistant to aminoglycoside antibiotics containing an hydroxyl group in the 3'-position. The compounds of the present invention are made as hereinafter described, beginning with seldomycin factor 5, the characteristics and preparation of which are described in U.S. Pat. No. 3,939,043.

DETAILED DESCRIPTION OF INVENTION

In summary, this invention relates particularly to a novel derivative of seldomycin factor 5, namely 3'-epi-seldomycin factor 5, which exhibits improved activity against bacteria known to be resistant to aminoglycoside antibiotics containing an hydroxyl group in the 3'-position. The invention further relates to a method for the inversion of the configuration of the hydroxyl group at $C_{3'}$ in seldomycin factor 5 and to intermediates involved in this method. The following process for the inversion of configuration of the hydroxyl group at $C_{3'}$ in seldomycin factor 5 has been found satisfactory.

The amine groups of seldomycin factor are protected with an "amine-protecting-group". This term is well recognized in the art. For the invention described herein the amine-protecting-group must be one which bonds to the amine directly via a carbonyl carbon. This includes such groups as alkoxycarbonyl, aryloxycarbonyl and aralkoxycarbonyl. The amine-protected seldomycin factor 5 is then converted into a sulfonate ester at the hydroxyl group attached to $C_{3'}$. It has been found that this may be done without involvement of the hydroxyl group attached to $C_5$.

Heating the 3'-sulfonate ester of the amine protected seldomycin factor 5 in an inert solvent such as dimethylformamide provides a compound of the type as described above by formula III.

Cleavage of the amine protecting groups with mild basic hydrolysis gives the compound of formula IV. Vigorous alkaline hydrolysis of this compound gives 3'-epi-seldomycin factor 5. The invention is further illustrated by the following examples:

EXAMPLE I

Seldomycin factor 5-per-N-ethoxycarbamate

A mixture of 10.12 grams of seldomycin factor 5 and 30 g of sodium carbonate are dissolved in 200 ml of distilled water and the solution cooled in an ice bath. A mixture of 30 ml of ethylchloroformate and 50 ml of acetone is added dropwise to this solution and the resulting mixture is allowed to stand at room temperature for two hours. The precipitated product is removed by filtration, washed twice with 200 ml portions of water and dried in vacuo to yield 16.8 g of seldomycin factor 5 per-N-ethoxycarbamate.

Microanalysis: C, 48.98; H, 7.12; N, 9.48%;
Calc. for $C_{36}H_{62}N_6O_{19}$: C, 48.97; H, 7.08; N, 9.52%.

EXAMPLE II

Seldomycin factor 5 per-N-ethoxycarbamate-3'-mesylate

A solution of 5 g of seldomycin factor 5 per-N-ethoxycarbamate in 120 ml of anhydrous pyridine is cooled in an ice bath and stirred as 1.3 ml of methanesulfonyl chloride are added. The mixture is allowed to warm to room temperature and to stand overnight. Solvent is removed and chromatography of the residue on a column of silica gel affords 4.0 grams of seldomycin factor 5 per-N-ethoxycarbamate-3'-mesylate.

In like manner, the compounds of 2–6 carbon atoms can be made by substituting the appropriate starting material, such as ethane sulfonyl chloride for example.

Microanalysis: C, 45,85; H, 6.81; N, 8.56; S, 3.70%; calcd. for $C_{37}H_{64}N_6O_{21}S$: C, 46.24; H, 6.71; N, 8.75; S, 3.34%.

EXAMPLE III

3'-epi-Seldomycin factor 5-1,3,6',2'',3''-penta-N-ethoxy-carbamate-2', 3'-cyclic-carbamate 3.5 grams of seldomycin factor 5 per-N-ethoxy carbamate-3'-mesylate are dissolved in 100 ml of anhydrous dimethyl formamide and the solution is heated at 90° C. overnight. Solvent is removed and chromatography of the residue on a column of silica gel affords 1.6 gram of seldomycin factor 5 per-N-ethoxy carbamate 2',3'-cyclic carbamate.

Microanalysis: C, 47.59; H, 6.73; N, 9.70%; calcd. for $C_{34}H_{56}N_6O_{18}$: C, 48.0; H, 6.75; N, 10.04%.

EXAMPLE IV

3'-epi-Seldomycin factor 5-1-N-3-N-ureide

A solution of 2.35 g of 3-epi seldomycin factor 5 per-N-ethoxycarbamate-2',3'-cyclic carbamate derivative in 250 ml of 1.9 N methanolic sodium hydroxide is heated under reflux overnight. The mixture is adjusted to pH 7 with 10 N sulfuric acid and solvent is removed. The residue is extracted with a mixture of chloroform (1 part) methanol (2 parts) and concentrated ammonium hydroxide (1 part by volume) and the extract is chromatographed over a column of silica gel to give 1 gram of 3'-epi-seldomycin factor 5-1N-3N-ureide. The sulfate salt of 3'-epi-seldomycin factor 5-1N-3N-ureide is prepared by treating a methanolic solution of the base with concentrated sulfuric acid. The solid precipitate is filtered off, washed well with methanol and dried to give the sulfate salt.

Microanalysis: C, 33.44; H, 6.30; N, 11.87%; calc. for $C_{19}H_{36}N_6O_8 \cdot 2 H_2SO_4 \cdot H_2O$: C, 33.04; H, 6.13; N, 12.17%.

EXAMPLE V

3'-epi-Seldomycin factor 5

Either 2.35 g of 3'-epi-seldomycin factor 5 per-N-ethoxy carbamate-2',3'-cyclic carbamate or 1.21 g of 3'-epi-seldomycin factor 5-1-N-3-N ureide in 50 ml of methanol is added to 50 ml of 12 N aqueous potassium hydroxide solution and the mixture is heated in a sealed tube at 135° C. for 16 hours. The reaction mixture is adjusted to pH 7 with 10 N sulfuric acid and solvent is removed. The residue is estracted with a mixture of chloroform (1 part), methanol (2 parts), and concentrated ammonium hydroxide (1 part by volume). The extract is chromatographed on a column of silica gel to give 1.6 g of 3'-epi-seldomycin factor 5.

These compounds are further characterized by their carbon magnetic resonance spectra, the signals of which are listed according to their probable assignments as follows:

Table 1*

| Carbon No. | Example I | Example II | Example III | Example IV | Example V |
|---|---|---|---|---|---|
| $C_1'$ | 99.6 | 99.4 | 96.8 | 102.1 | 102.7 |
| $C_2'$ | 57.6 | 59.6 | 51.2 | 51.6 | 51.9 |
| $C_3'$ | 64.5 | 77.6 | 71.7 | 68.3 | 68.0 |
| $C_4'$ | 37.0 | 38.0 | 27.2 | 35.3 | 35.3 |
| $C_5'$ | 66.7 | 65.8 | 65.3 | 66.1 | 66.0 |
| $C_6'$ | 44.4 | 43.8 | 44.0 | 45.6 | 45.6 |

Table 1*-continued

| Carbon No. | Example I | Example II | Example III | Example IV | Example V |
|---|---|---|---|---|---|
| $C_1$ | 50.6 | 50.7 | 50.9 | 48.1 | 51.0 |
| $C_2$ | 34.9 | 35.1 | 34.6 | 18.2 | 36.6 |
| $C_3$ | 49.9 | 49.8 | 49.5 | 45.6 | 50.0 |
| $C_4$ | 82.4 | 82.7 | 81.9 | 76.2 | 88.8 |
| $C_5$ | 74.7 | 74.6 | 74.8 | 70.8 | 75.1 |
| $C_6$ | 79.6 | 79.6 | 78.8 | 80.1 | 87.0 |
| $C_1''$ | 96.9 | 96.9 | 96.5 | 98.0 | 100.0 |
| $C_2''$ | 54.4 | 54.4 | 54.3 | 55.5 | 56.2 |
| $C_3''$ | 53.1 | 53.2 | 53.3 | 55.5 | 54.8 |
| $C_4''$ | 76.3 | 76.3 | 76.4 | 80.1 | 80.3 |
| $C_5''$ | 59.5 | 59.6 | 59.5 | 60.8 | 60.8 |
| $OCH_3$ | 57.6 | 57.6 | 57.7 | 58.8 | 58.6 |

*Only peaks assigned to ψ-trisaccharide carbons are shown. The spectra are described as parts-per-million (ppm) downfield from tetramethylsilane. Dimethylsulfoxide was used as a solvent for the compounds of Examples I, II and III and deuterium oxide was used as a solvent for the compounds of Examples IV and V.

EXAMPLE VI

Seldomycin Factor 5 per-N-ethoxycarbamate-3'-benzylsulfonate

A solution of 451 mg of seldomycin factor 5 per-N-ethoxycarbonyl derivative in 30 ml of anhydrous pyridine is cooled in an ice bath and stirred as 477 mg of benzylsulfonyl chloride are added. The mixture is allowed to warm to room temperature and to stand overnight. Solvent is removed and chromatography of the residue on a column of silica gel affords 439 mg of seldomycin factor 5 per-N-ethoxycarbamate-3'-benzylsulfonate.

EXAMPLE VII

Seldomycin Factor 5 per-N-ethoxycarbamate-3'-p-bromophenyl-sulfonate

A solution of 451 mg of seldomycin factor 5 per-N-ethoxycarbonyl derivative in 30 ml of anhydrous pyridine is cooled in an ice bath and stirred as 255 mg of p-bromo benzene sulfonyl chloride are added. The mixture is allowed to warm to room temperature and to stand overnight. Solvent is removed and chromatography of the residue on a column of silica gel afford 401 mg of seldomycin factor 5 per-N-ethoxycarbamate-3'-p-bromophenylsulfonate.

Raman spectrum 1183 cm$^{-1}$.

EXAMPLE VIII

Seldomycin Factor 5 per-N-ethoxycarbamate-3'-p-toluenesulfonate

A solution of 451 mg of seldomycin factor 5 per-N-ethoxycarbonyl derivative in 30 ml of anhydrous pyridine is cooled in an ice bath and stirred as 477 mg of p-toluene sulfonyl chloride are added. The mixture is allowed to warm to room temperature and to stand overnight. Solvent is removed and chromatography of the residue on a column of silica gel affords 378 mg of seldomycin factor 5 per-N-ethoxycarbamate-3'-tosylate.

Raman spectrum 1180 cm$^{-1}$.

TABLE 2

| | CMR Data of 3'-Sulfonates | | |
|---|---|---|---|
| | Compound | | |
| | Example VI | Example VII | Example VIII |
| $C_1'$ | 99.6 | 99.1 | 99.2 |
| $C_2'$ | 54.6 | 54.1 | 54.2 |
| $C_3'$ | 77.9 | 79.3 | 78.1 |
| $C_4'$ | 34.9 | 35.0 | 34.9 |
| $C_5'$ | 65.9 | 65.9 | 65.9 |

TABLE 2-continued

| | CMR Data of 3'-Sulfonates | | |
|---|---|---|---|
| | Compound | | |
| | Example VI | Example VII | Example VIII |
| $C_6'$ | 43.9 | 43.9 | 43.8 |
| $C_1$ | 50.6 | 50.7 | 50.7 |
| $C_2$ | 35.0 | 35.0 | 34.9 |
| $C_3$ | 49.9 | 49.7 | 49.7 |
| $C_4$ | 82.8 | 81.9 | 82.1 |
| $C_5$ | 74.8 | 74.3 | 74.4 |
| $C_6$ | 79.9 | 79.6 | 79.6 |
| $C_1''$ | 97.0 | 96.9 | 96.9 |
| $C_2''$ | 54.5 | 54.4 | 54.4 |
| $C_3''$ | 53.1 | 53.2 | 53.2 |
| $C_4''$ | 76.3 | 76.4 | 76.3 |
| $C_5''$ | 59.6 | 59.5 | 59.5 |
| $OCH_3$ | 57.6 | 57.7 | 57.6 |

3'-Epi-seldomycin factor 5 was tested for antimicrobial activity against Gram-positive and Gram-negative bacteria in an agar dilution test. Results are given in mic values (minimum inhibitory concentrations) expressed in micrograms/ml as follows:

Table 3

| Organism | Strain | Seldomycin 5 base | 3'-epi-Seldomycin 5 |
|---|---|---|---|
| Facherichia coli | ATCC 26 | 0.13 | 1.06 |
| E. coli | R5 | >100 | 12.5 |
| E. coli | R20 | 100 | 8.13 |
| E. coli | R18 | 0.78 | 0.83 |
| Staphylococcus aureus | ATCC 6538P | 0.16 | 0.63 |
| Streptococcus faecalis | ATCC 10541 | 25 | >100 |
| Proteus vulgaris | ATCC 6897 | 0.31 | 2.8 |
| Salmonella typhi | ATCC 9992 | 0.16 | 1.4 |
| Shigella sonnei | ATCC 9290 | 0.31 | 2.0 |
| Klebsiella pneumoniae | ATCC 10031 | 0.04 | 0.4 |
| Pseudomonas aeruginosa | BMH #1 | 17.5 | 11.3 |
| Ps. aeruginosa | KY 8512 | 25 | 25 |

What is claimed is:
1. A compound of the formula

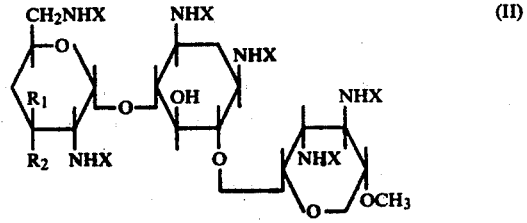

(II)

wherein when $R_1$ is OH or $RSO_3$, $R_2$ is H and when $R_1$ is H, $R_2$ is OH and wherein R is a member of the group consisting of alkyl of 1-6 carbon atoms, phenyl, phenyl substituted by halo, nitro, toluyl, naphthyl and benzyl and wherein X is a carbonyl containing amine-protecting group.

2. A compound of claim 1 wherein the carbonyl containing amine-protecting group is a member of the group consisting of alkoxy carbonyl, aryloxy carbonyl and aralkyloxy carbonyl.

3. A compound selected from the group consisting of seldomycin factor 5 per-N-ethoxycarbamate-3'mesylate, 3'-epi-seldomycin factor 5-1, 3, 6', 2'', 3''-penta-N-ethoxycarbamate-2', 3'-cyclic-carbamate, 3'-epi-seldomycin factor 5-1-N-3-N-ureide and 3'-epi-seldomycin factor 5.

4. The compound of claim 3: 3'-epi-seldomycin factor 5.

5. The compound of claim 3: 3'-epi-seldomycin factor 5-1, 3, 6', 2'', 3''-penta-N-ethoxycarbamate-2', 3'-cyclic-carbamate.

6. The compound of claim 3: 3'-epi-seldomycin factor 5-1-N-3-N-ureide.

7. The compound of claim 3: seldomycin factor 5 per-N-ethoxycarbamate-3'-mesylate.

* * * * *